United States Patent
Knobloch

(10) Patent No.: US 10,252,033 B2
(45) Date of Patent: Apr. 9, 2019

(54) DEVICE FOR COVERING A CATHETER ACCESS TO A HUMAN OR ANIMAL BODY, IN PARTICULAR A CENTRAL VENOUS CATHETER ACCESS

(71) Applicant: PFM MEDICAL AG, Cologne (DE)

(72) Inventor: Helmut Knobloch, Kreuzau (DE)

(73) Assignee: PFM MEDICAL AG, Cologne (DE)

(*) Notice: Subject to any disclaimer, the term of this patent is extended or adjusted under 35 U.S.C. 154(b) by 0 days.

(21) Appl. No.: 14/373,076

(22) PCT Filed: Jan. 16, 2013

(86) PCT No.: PCT/EP2013/000111
§ 371 (c)(1),
(2) Date: Jul. 18, 2014

(87) PCT Pub. No.: WO2013/107634
PCT Pub. Date: Jul. 25, 2013

(65) Prior Publication Data
US 2014/0364810 A1    Dec. 11, 2014

(30) Foreign Application Priority Data
Jan. 18, 2012   (DE) .................... 20 2012 000 408 U

(51) Int. Cl.
*A61M 25/02*   (2006.01)
(52) U.S. Cl.
CPC ....... *A61M 25/02* (2013.01); *A61M 2025/028* (2013.01); *A61M 2025/0246* (2013.01);
(Continued)
(58) Field of Classification Search
CPC .......... A61M 25/02; A61M 2025/0273; A61M 2025/0246; A61M 2025/028;
(Continued)

(56) References Cited

U.S. PATENT DOCUMENTS 3,194,235 A * 7/1965 Cooke ................... A61M 25/02
128/888
4,633,863 A * 1/1987 Filips ................... A61M 25/02
128/846
(Continued)

FOREIGN PATENT DOCUMENTS

DE   3643985    12/1987
DE   19602467   8/1996
(Continued)

OTHER PUBLICATIONS

Affix Definition, 2016, Dictionary.com LLC.*
(Continued)

*Primary Examiner* — Bradley J Osinski
*Assistant Examiner* — Nilay J Shah
(74) *Attorney, Agent, or Firm* — Grossman, Tucker, Perreault & Pfleger, PLLC

(57) ABSTRACT

The invention relates to device for covering a catheter access to a human or animal body, particular a central venous catheter access, comprising a wedge-shaped guiding element, which is arranged between the catheter of the catheter access and the surface of the human or animal body during use, in order to guide the catheter relative to the entry point into the human or animal; and a self-adhesive covering element for covering and fixing the wedge-shaped guiding element and the catheter in the area of the entry point into the human or animal body, which self-adhesive covering element is affixed to the surface of the human or animal body during use in such a way, that the catheter and the wedge-shaped guiding element are at least partially arranged between the covering element and the surface of the human and/or animal body.

38 Claims, 2 Drawing Sheets

(52) U.S. Cl.
 CPC ............... *A61M 2025/0266* (2013.01); *A61M 2025/0273* (2013.01)

(58) Field of Classification Search
 CPC .. A61M 2025/0266; A61M 2025/0213; A61M 2025/0253
 See application file for complete search history.

(56) References Cited

U.S. PATENT DOCUMENTS

| | | | |
|---|---|---|---|
| 4,898,587 A | | 2/1990 | Mera |
| 5,112,313 A | * | 5/1992 | Sallee ................ A61M 25/0612 604/180 |
| 5,685,859 A | * | 11/1997 | Kornerup .............. A61M 25/02 604/179 |
| 5,840,052 A | | 11/1998 | Johns |
| 6,032,670 A | * | 3/2000 | Miller ................... A61B 19/08 128/849 |
| 6,201,164 B1 | * | 3/2001 | Wulff ................... A61K 9/0014 602/41 |
| 7,137,968 B1 | | 11/2006 | Burrell et al. |
| 2009/0149814 A1 | * | 6/2009 | Bailey ................... A61M 25/02 604/180 |
| 2011/0166492 A1 | | 7/2011 | Holm et al. |

FOREIGN PATENT DOCUMENTS

| | | |
|---|---|---|
| DE | 60125024 | 6/2007 |
| DE | 102008053335 | 5/2010 |
| EP | 1698368 | 9/2006 |
| WO | 97/21459 | 6/1997 |

OTHER PUBLICATIONS

International Search Report from corresponding PCT Appln. No. PCT/EP2013/000111 dated Mar. 7, 2013. English translation attached.

* cited by examiner

DEVICE FOR COVERING A CATHETER ACCESS TO A HUMAN OR ANIMAL BODY, IN PARTICULAR A CENTRAL VENOUS CATHETER ACCESS

CROSS REFERENCE TO RELATED APPLICATIONS

This is the U.S. National Phase Application under 35 U.S.C. § 371 of International Patent Application No. PCT/EP2013/000111 filed Jan. 16, 2013, which claims the benefit of German Patent Application No. 20 2012 000 408.5 filed on Jan. 18, 2012, the disclosures of which are incorporated by reference herein in their entirety.

FIELD OF THE INVENTION

The invention relates to a device for covering a catheter access to a human or animal body, particular a central venous catheter access.

BACKGROUND

A central venous catheter (CVC), also referred to as a central venous line or central venous access, is for example inserted via a vein of the upper body part into the venous system, wherein the end of the central venous catheter ends in the upper or lower cava of the right atrium of the heart. Alternatively a central venous catheter can be inserted at another location into the venous system of the human or animal body, like the leg vein (vena famoralis).

Using the central venous catheter for example highly concentrated electrolytic solutions and nutrium solutions can be inserted into the venous system. Furthermore, a central venous catheter permits to measure the central venous pressure as an indication for the intravascular volume (which equals to the blood volume).

A central venous catheter can comprise up to six lumina, wherein typically two or three lumina are used in a central venous catheter. Using the individual lumina for example parenteral nutritions, catecholamines and antibiotics can be inserted into the venous systems in parallel, without the danger of an incompatibility between the single substances.

The usage of a central venous catheter can lead to a colonization, particular at the entry point of the central venous catheter into the human or animal body with bacteria or fungi. These bacteria or fungi can cause a so called central venous catheter associated bacteraemea, fungaemea or a catheter related blood screen infection (CRBSI), which can be life-threatening for patients.

From the prior art it is known to fix the catheter access relative to the entry point into the human or animal body and to cover the entry point using a self-adhesive plaster. Furthermore, for example the self-adhesive plaster which is distributed by company 3M Medica under the name "Tegaderm™ CHG", comprises a gel pad with an anti-microbial activity, whereby a colonization with bacteria or fungi should be prevented.

The self-adhesive plaster "Glycosave Soft" distributed by company Mediglobe comprises an anti-microbial gel pad in the area of the entry point of the catheter to prevent a colonization with bacteria or fungi.

The devices known from the prior art for covering a catheter access to a human or animal body, particular a central venous catheter access, have the disadvantage, that the catheter is bent in the area of the entry point, whereby the cross section of the lumina within the catheter is changed, which leads to a change in the flow rate.

SUMMARY

It is therefore an object of the present invention to provide a device for covering a catheter access to a human or animal body (particular a central venous catheter access), which avoids as far as possible a bending of the catheter in the area of the entry point into the human or animal body.

This object is solved by a device for covering a catheter access to a human or animal body, particular a central venous catheter access, comprising a wedge-shaped guiding element, which is arranged between the catheter of the catheter access and the surface of the human or animal body during use, in order to guide the catheter relative to an entry point into the human or animal body; and a self-adhesive covering element for covering and fixing the wedge-shaped guiding element and the catheter in the area of the entry point into the human or animal body, which self-adhesive covering element is fixed to the surface of the human or animal body during use in such a way, that the catheter and the wedge-shaped guiding element are at least partially arranged between the covering element and the surface of the human or animal body.

The wedge-shaped guiding element is therefore arranged in such a way, that the tapered end of the wedge-shaped guiding element is arranged in the area of the entry point of the catheter into the human or animal body. Thereby it is achieved that the catheter extends in a sharp angle to the entry point into the human or animal body and after the entry into the human or animal body further extends into the vein system without a bending at the entry point. The self-adhesive covering element is used to avoid a colonization with bacteria or fungi and to fix the wedge-shaped guiding element and the catheter in the area of the entry point into the human or animal body relative to the human or animal body.

According to a variant of the invention the device further comprises a fixing element, which is located during its use between the catheter and the self-adhesive covering element and designed for fixing the catheter relative to the entry point and the self-adhesive covering element. The catheter is therefore fixed in the area of the entry point into the human or animal body using the wedge-shaped guiding element and the further fixing element and afterwards relative to the human or animal body fixed and covered using the self-adhesive covering element. Furthermore the additional fixing element has the advantage that the self-adhesive covering element is not in direct contact with the catheter, which can lead to complications during the removal of the self-adhesive covering element from the human or animal body, since the catheter could stick to the self-adhesive covering element during the removal from the human or animal body.

According to a further variant of the invention the wedge-shaped guiding element, the fixing element and/or the self-adhesive covering element are at least partially gel-like. This has the advantage that the single element can better conform to the outline of the catheter and/or the human or animal body, thereby the catheter is particularly in the area of the entry point into the human or animal body fixed more securely. Preferably therefore a gel comprising glycerin is used.

According to a preferred variant of the invention the self-adhesive covering element, the fixing element and/or the wedge-shaped guiding element are at least partially transparent. Particularly these elements are transparent in such a way, that the entry point of the catheter into the human or animal body is visible without a removal of the inventive device, so that it can be for example determined if the entry point is inflamed.

According to a practical variant of the invention the self-adhesive covering element, the fixing element and/or the wedge-shaped guiding element have an anti-microbial, anti-bacterial and/or anti-fungal effect.

According to a further preferred variant of the invention the self-adhesive covering element, the fixing element and/or the wedge-shaped guiding element are moisture absorbing, waterproof and/or breathable. Moisture absorbing elements have the advantage, that these can absorb fluids eventually exiting from the entry point of the catheter into the human or animal body, so that these can have no negative influence on the entry point into the human or animal body or to the human or animal body in the area of the entry point. Preferably the moisture absorbing elements are designed in such a way, that the absorbed fluid is stored and cannot leave the moisture absorbing element. Waterproof elements avoid an invasion of fluids into the entry point into the human or animal body, which may be contaminated with bacteria. Breathable elements allow a water vapor and oxygen exchange in the areas, in which the inventive device is fixed to the surface of the human or animal body, whereby an irritation of the surface of the human or animal body in the area of the inventive device can be as far as possible avoided. Preferably the self-adhesive covering element is waterproof and breathable, whereas the fixing element and the wedge-shaped guiding element are moisture absorbing.

In a particularly preferred variant of the invention the wedge-shaped guiding element and/or the fixing element are self-adhesive, particularly on the surface located towards the surface of the human or animal body during use. Such an embodiment has the advantage, that after the catheter is inserted into a human or animal body the wedge-shaped guiding element can be fixed to the surface of the human or animal body in the area of the entry point of the catheter into the human or animal body and afterwards eventually the further fixing element can be fixed relative to wedge-shaped guiding element and the catheter located thereon and afterwards the wedge-shaped guiding element, the catheter and the additional fixing element can be fixed relative to the surface of the human or animal body using the self-adhesive covering element.

Advantageously the used adhesives are latex-free, particularly hypoallergenic, for example an acrylate adhesive. Thereby an especially tolerability for the human or animal body is achieved.

Preferably the wedge-shaped guiding element, the fixing element and/or the self-adhesive covering element consist of polyurethane, polypropylene and/or polyethylene.

According to a further variant of the inventive device the wedge-shaped guiding element has an angle between 1 degree and 30 degree, preferably between 3 degree and 20 degree and particularly between 5 degree and 10 degree. The angle defines the inclination of the wedge-shaped guiding element. By the mentioned angles an especially smooth transition of the catheter into the venous system of the human or animal body is achieved, so that the catheter is not bent in the area of the entry point in such a way that the cross section of the lumina within the catheter is changed.

In a further variant of the inventive device the wedge-shaped guiding element has a recess in the area of converging surfaces, such that that two protrusions are created in this area. Preferably the recess is designed in such a way, that the entry point into the human or animal body is located in the area of the recess during the use of the device and the protrusions at least partially enclosed the entry point laterally. Thereby a better fixing of the catheter relative to the entry point into the human or animal body is achieved. For example the recess is triangular shaped and the tip of the triangular shape recess is located away from the converging surface of the wedge-shaped guiding element.

Advantageously the wedge-shaped guiding element, the fixing element and/or the self-adhesive covering element are adapted to a particular catheter size and/or catheter profile, for example by cavities corresponding to the size or profile of the catheter for receiving the outline of the catheter.

According to a further variant of the invention the fixing element comprises recesses or cavities on the surface located towards the human or animal body during use for the entry point, the catheter and/or the wedge-shaped guiding element.

Since the fixing element is thereby adapted to the profiles of the surrounding elements or the catheter and the entry point, a better fixing of the catheter relative to the entry point into the human or animal body is achieved.

Preferably the self-adhesive covering element comprises lateral wings, which laterally enclose the catheter at the end opposite to the entry point, preferably in the area where a hose can be connected to the catheter. Thereby the self-adhesive covering element can be arranged on the wedge-shaped guiding element and the optional additional fixing element, even if the catheter is already inserted into the human or animal body and connected to a hose.

Furthermore the self-adhesive covering element is particularly designed in such a way, that the self-adhesive covering element is during the use of an additional fixing element not in direct contact with the catheter.

Due to the fixing of the catheter access relative to the human or animal body the covering of the entry point of the catheter into the human or animal body the inventive device is suitable for a long term application, particularly for gestation periods up to ten days, preferably eight days.

The inventive device is usable besides a central venous catheter access for a peripheral introduced central catheter, an arterial catheter, a port catheter system or an epidural catheter.

BRIEF DESCRIPTION OF THE DRAWINGS

In the following the invention is explained with respect to the embodiments shown in the figures. It is shown in.

DETAILED DESCRIPTION

Figure 1:
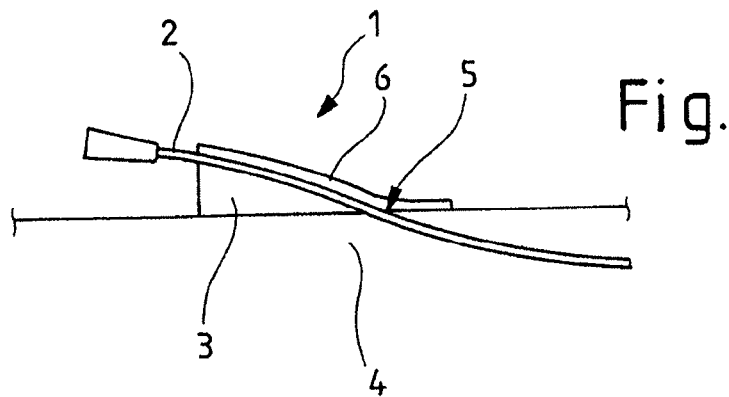
FIG. 1 is a lateral sectional view of an inventive device.

FIG. 1 shows an inventive device 1 for covering a catheter access to a human or animal body 4, particular a central venous catheter access. The device 1 comprises a wedge-shaped guiding element 3, which is arranged between the catheter 2 of the catheter access and the surface of the human or animal body 4 during use, in order to guide the catheter 2 relative to an entry point 5 into the human or animal body 4. The inventive device 1 further comprises a self-adhesive covering element 6 for covering and fixing the wedge-shaped guiding element 3 and the catheter 2 in the area of the entry point 5 into the human or animal body 4. The self-adhesive covering element 6 is affixed to the surface of the human or animal body 4 during use in such a way that the catheter 2 and the wedge-shaped guiding element 3 are at least partially arranged between the covering element 6 and the surface of the human or animal body 4.

Thereby using the inventive device 1 for covering the catheter access to a human or animal body 4, particular a central venous catheter access, the catheter 2 is guided in the area of the entry point 5 into the human or animal body 4 in such a way, that the catheter 2 is not bent, particularly in such a way that the cross sectional of the lumina within the catheter 2 are not changed. Furthermore, the entry point 5 into the human or animal body 4 is protected by the self-adhesive covering element 6 against a colonization by bacteria or fungi.

The wedge-shaped guiding element 3 of FIG. 1 is gel-like, so that it can conform to the surface of the human or animal body 4. A gel-like design of the wedge shape guiding element 3 has the further advantage, that the wedge-shaped guiding element 3 can conform to the catheter 2. The self-adhesive covering element 6 of FIG. 1 is as flexible as possible, so that it can conform to the outline of the wedge-shaped guiding element 3, the catheter 2 and the surface of the human or animal body 4.

The self-adhesive covering element 6 and the wedge-shaped guiding element 3 of FIG. 1 are, at least partially transparent, particular in the area of the entry point 5 of the catheter 2 into the human or animal body 4. Thereby, the entry point 5 of the catheter 2 into the human or animal body 4 can be examined with respect to eventually occurring abnormalities, like e.g. inflammation, during the whole period of use, without the need of a removal of the self-adhesive covering 6 and/or the wedge shape guiding element 3.

The self-adhesive covering element 6 and the wedge-shaped guiding element 3 of FIG. 1 have a anti-microbial, anti-bacterial and/or anti-fungal effect, to avoid a colonization of the entry point 5 into the human or animal body 4 by bacteria or fungi. Thereby the risk of a central venous catheter access associated bacteraeme or fungaemea or a catheter sepsis can be considerably reduced.

The wedge-shaped guiding element 3 of FIG. 1 is moisture absorbing, to absorb fluid eventually exiting from the entry point 5 of the catheter 2 into the human or animal body 4. Furthermore the self-adhesive covering element 6 of FIG. 1 is waterproof and breathable, whereby on the one hand an entry of fluids is avoided and on the other hand water vapor and oxygen exchange of the human or animal body 4 in the direction of environment is possible.

Preferably the wedge-shaped guiding element 3 of FIG. 1 is self-adhesive, particularly on the surface located towards a surface of the human or animal body 4 during use. Thereby the wedge-shaped guiding element 3 can be fixed relative to the entry point 5 of the catheter 2 into the human or animal body 4 before it is fixed using the self-adhesive covering element 6.

All adhesive mentioned with respect to the inventive device 1 are latex-free and hypoallergenic, to treat the surface of the human or animal body 4 with care.

The wedge-shaped guiding element 3 and the self-adhesive covering element 6 of FIG. 1 consist for example of polyurethane.

Figure 2:
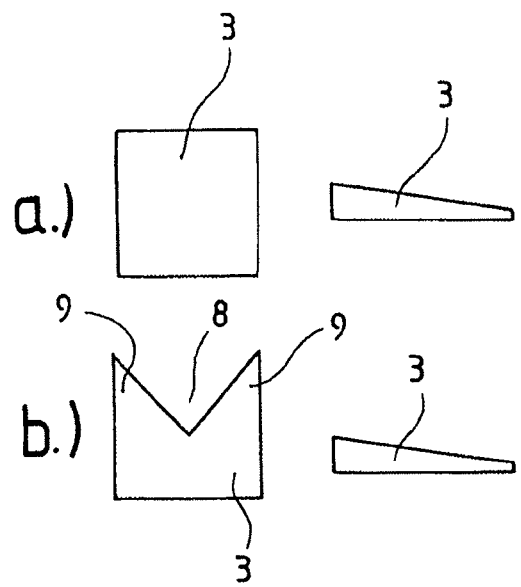
FIG. 2a is a wedge-shaped guiding element for use with an inventive device.
FIG. 2b is a further wedge-shaped guiding element for use with an inventive device.

As can been seen especially in FIGS. 2a and 2b the wedge-shaped guiding element 3 has an angle between 1 degree and 30 degrees, preferably between 3 degree and 20 degree and particularly between 5 degree and 10 degree. Wherein the angle defines the inclination of the wedge-shaped guiding element 3.

In the embodiment according to FIG. 2b the wedge-shaped guiding element 3 comprises a recess 8 in the area of converging surfaces, such that two protrusions 9 are created in this area. The wedge-shaped guiding elements 3 according to FIG. 2b is located in such a way on the surface of the human or animal body 4, that the entry point 5 of the catheter 2 into the human or animal body 4 is located in the area of the recess 8 and the two protrusions 9 at least partially enclose the entry point 5 of the catheter 2 into the human or animal body 4 laterally.

The recess 8 of the wedge-shaped guiding elements 3 of FIG. 2b is triangular shaped, wherein the tip of the triangular shaped recess 8 is located away from the converging surfaces of the wedge-shaped guiding elements 3.

Figure 3:
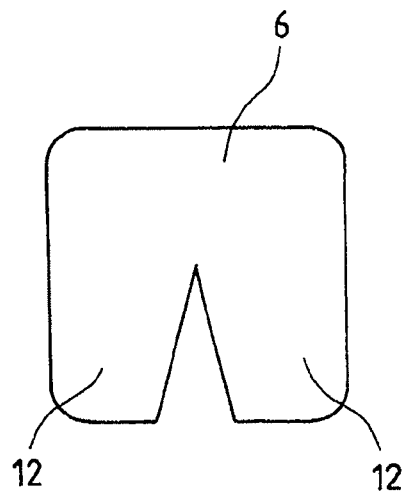
FIG. 3 is a self-adhesive covering element for use with an inventive device.

FIG. 3 shows a detailed view of the self-adhesive covering element 6 for covering and fixing the wedge-shaped guiding elements 3 and the catheter 2 in the area of the entry point 5 into the human or animal body 4. The self-adhesive covering element 6 of FIG. 3 is fixed during the use in such a way to the surface of the human or animal body 4, that the catheter 2 and the wedge-shaped guiding element 3 are at least partially between the covering element 6 and the surface of the human or animal body 4. The self-adhesive covering element 6 of FIG. 3 comprises two lateral wings 12, which laterally enclose the catheter 2 at the end opposite to the entry point 5. Thereby the self-adhesive covering element 6 can be arranged on the wedge-shaped guiding element 3 and the catheter 2 even if the catheter 2 is inserted into the human or animal body 4 and the catheter 2 is already connected to a hose.

Figure 4:
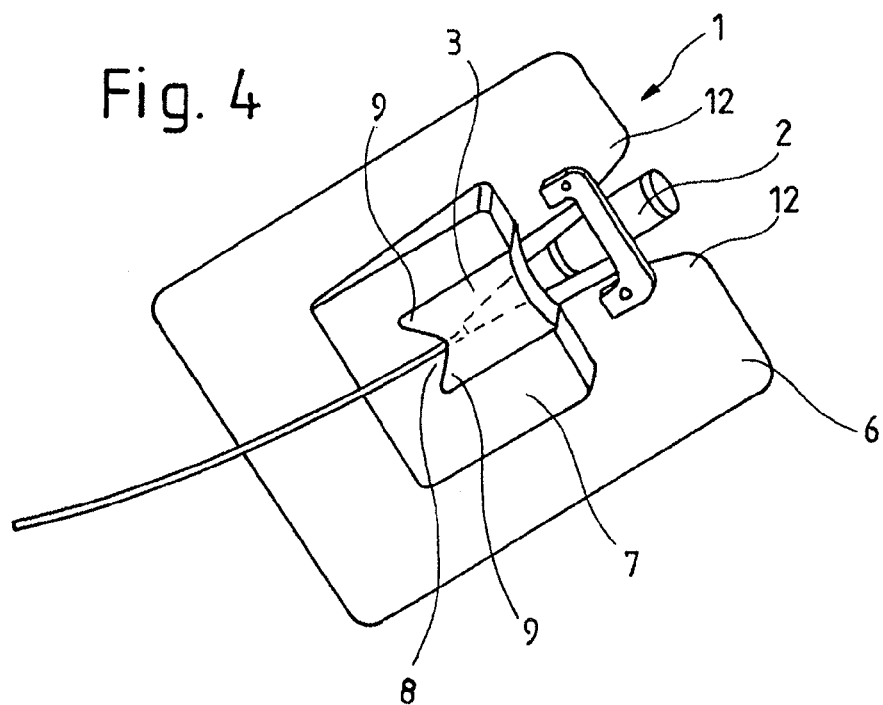
FIG. 4 is a perspective view of a further inventive device from the direction of the animal or human body.

In FIG. 4 a second variant of the inventive device 1 for covering a catheter access to a human or animal body 4, particular a central venous catheter access, is shown. The device 1 of FIG. 4 comprises a wedge-shaped guiding element 3, which is arranged between the catheter 2 of the catheter access and the surface of the human or animal body 4 during use, to guide the catheter 2 relative to the entry point 5 into the human or animal body 4.

The device 1 of FIG. 4 further comprises a fixing element 7, which is arranged during use between the catheter 2 and self-adhesive covering element 6 and is designed for fixing the catheter 2 relative to the entry point 5 and the self-adhesive covering element 6.

The self-adhesive covering element 6 of the device 1 according to FIG. 4 is used for covering and fixing the wedge-shaped guiding element 3, the catheter 2 and the fixing element 7 particularly in the area of the entry point 5 into the human or animal body 4. The self-adhesive covering element 6 is fixed during use in such a way that the wedge-shaped guiding element 3 is arranged between the catheter 2 and the surface of the human or animal body and the fixing element 7 is located between the catheter 2 and the self-adhesive covering element 6.

The wedge-shaped guiding element 3 and the fixing element 7 of FIG. 4 are gel-like, so that these can better conform to the outline of the human or animal body 4 or the catheter 2. The self-adhesive covering element 6, the fixing element 7 and the wedge-shaped guiding element 3 of FIG.

4 are at least in the area of the entry point 5 of the catheter 2 into the human or animal body 4 transparent, to examine the entry point 5 of the catheter 2 into the human or animal body 4 during the use of the inventive device 1.

Advantageously the self-adhesive covering element 6, the fixing element 7 and the wedge-shaped guiding element 3 have an anti-microbial, anti-bacterial and/or anti-fungal effect, to protect the entry point 5 of the catheter 2 into the human or animal body 4 against a colonization by bacteria and/or fungi.

The self-adhesive covering element 6 of FIG. 4 is waterproof and breathable, to avoid an entry of fluids into the entry point 5 of the catheter 2 into the human or animal body 4 and at the same time take care of the surface of the human or animal body 4 in the area of the entry point 5 of the catheter 2 into the human or animal body 4.

The fixing element 7 and the wedge-shaped guiding element 3 of FIG. 4 are preferably moisture absorbing, to absorb eventually exiting fluids from the entry point 5 of the catheter 2 into the human or animal body 4.

Furthermore, the wedge-shaped guiding element 3 and the fixing element 7 are self-adhesive, particularly on the surface located towards the surface of the human or animal body 4 during use. Thereby the wedge-shaped guiding element 3 and the fixing element 7 can be fixed relative to the surface of the human or animal body 4 before the self-adhesive covering element 6 is applied to the wedge-shaped guiding element 3 or the fixing element 7.

The used adhesives of the inventive device 1 of FIG. 4 are latex-free and hypoallergenic, to take care of the surface of the human or animal body 4.

The wedge-shaped guiding element 3, the fixing element 7 and the self-adhesive covering element 6 consists of polyurethane.

As can be especially seen from the detailed view of the wedge-shaped guiding element 3 of FIG. 4 the wedge-shaped guiding element 3 has an angle between one 1 degree and 30 degree, preferably between 3 degree and 20 degree and particularly between 5 degree and 10 degree. The angle defines the inclination of the wedge-shaped guiding element 3.

Figure 5:
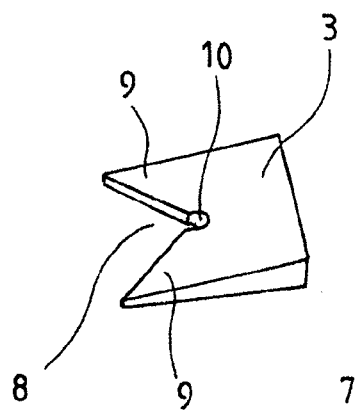
FIG. 5 is a detailed view of the wedge-shaped guiding element of FIG. 4.

The wedge-shaped guiding element 3 has a recess 8 in the area of converging surfaces, such that two protrusions 9 are created in this area, as shown in FIG. 5. The recess 8 is designed in such a way, that the entry point 5 into the human or animal body 4 is located in the area of the recess 8 during the use of the device 1 of FIG. 4 and the protrusions 9 at least partially enclose the entry point 5 laterally. Thereby a better fixing of the catheter 2 relative to the entry point 5 into the human or animal body is achieved. The recess 8 is triangular shaped, wherein the tip of the triangular shaped recess is located away from the converging surfaces of the wedge-shaped guiding element 3.

The wedge-shaped guiding element 3 and the fixing element 7 are adapted to a particular catheter size and/or catheter profile, for example by cavities 10, 11 corresponding to the size or profile of the catheter 2 for receiving the outline of the catheter 2.

Figure 6:
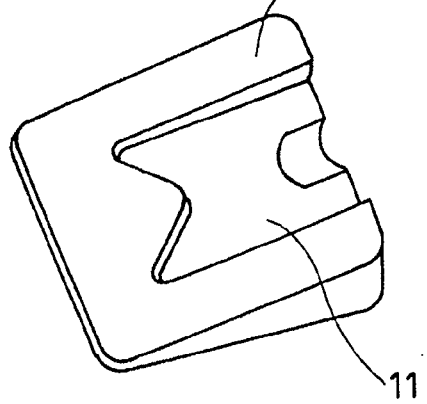
FIG. 6 is a detailed view of the fixing element of FIG. 4.

Particularly the fixing element 7 has recesses or cavities 11 on the surface located towards a human or animal body 4 for the entry point 5, the catheter 2 and/or the wedge-shaped guiding element 3, as can be seen in the detailed view of FIG. 6. The fixing element 7 shown in FIG. 6 is also wedge-shaped as with the guiding element 3. Alternatively the fixing element 7 can have a flat outline.

The self-adhesive covering element 6 of FIG. 4 has lateral wings 12, which laterally enclose the catheter 2 at the end opposite to the entry point 5, preferably in the area where a hose can be connected to the catheter 2. The self-adhesive covering element 6 of the FIG. 4 corresponds therefore to the self-adhesive covering element 6 of FIG. 3. By such a design the self-adhesive covering element 6 can be arranged on the wedge-shaped guiding element 3 and the additional fixing element 7, even in case the catheter 2 is inserted into the human or animal body 4 and the catheter 2 is already connected to a hose. Furthermore the self-adhesive covering element 6 is built in such a way, that the self-adhesive covering element 6 is not in direct contact with the additional fixing element 7 during use.

Because of the fixing of the catheter access relative to the human or animal body 4 and covering of the entry point 5 of the catheter 2 into the human or animal body 4 the inventive device is suitable for long term applications, particularly for a gestation period of up to ten days.

Furthermore, the inventive device 1 is suitable next to a central venous catheter access for a peripheral inserted central catheter, an arterial catheter, port catheter systems and epidural catheter.

REFERENCE LIST 1 device
2 catheter
3 wedge-shaped guiding element
4 human or animal body
5 entry point
6 self-adhesive covering element
7 fixing element
8 recess in the wedge-shaped guiding element
9 protrusions of the wedge-shaped guiding element
10 cavity for the outline of the catheter
11 cavity or recess for the fixing element
12 wing

What is claimed is:

1. A device for covering a catheter access of a catheter to a body, comprising:
   a wedge-shaped guiding element configured to be arranged between the catheter of the catheter access and a surface of the body, and configured such that the catheter rests on the wedge-shaped guiding element and is supported along a slope of the wedge-shaped guiding element, and wherein the wedge-shaped guiding element is configured to guide the catheter relative to an entry point into the body;
   a self-adhesive covering element which covers and fixes the wedge-shaped guiding element and the catheter in an area of the entry point into the body;
      wherein at least a portion of the self-adhesive covering element is configured to be adhesively affixed directly to the surface of the body; and
      wherein the catheter and the wedge-shaped guiding element are configured to be at least partially arranged between the covering element and the surface of the body; and
   a self-adhesive fixing element configured to be arranged between the catheter and the self-adhesive covering element, wherein the self-adhesive fixing element is wedge-shaped and at least a portion of the self-adhesive fixing element is configured to be adhesively affixed directly to the surface of the body and wherein the fixing element is configured to fix the catheter relative to the entry point and the self-adhesive covering element; and wherein the wedge-shaped guiding element has a tapered end, a length and opposing surfaces, the opposing surfaces comprising a first surface which faces towards the self-adhesive covering element, and a second surface to face towards the surface of the body, and wherein the first and the second surfaces of the wedge-shaped guiding element comprise converging surfaces which converge towards the tapered end along the length of the wedge-shaped guiding element.

2. The device according to claim 1, wherein at least one of the wedge-shaped guiding element, the fixing element and the self-adhesive covering element are at least partially gel-like.

3. The device according to claim 2, wherein the fixing element is gel-like.

4. The device according to claim 3, wherein the fixing element comprises a gel.

5. The device according to claim 1, wherein at least one of the self-adhesive covering element, the fixing element and the wedge-shaped guiding element are at least partially transparent.

6. The device according to claim 1, wherein at least one of the self-adhesive covering element, the fixing element and the wedge-shaped guiding element have at least one of an anti-microbial, anti-bacterial and anti-fungal effect.

7. The device according to claim 1, wherein at least one of the self-adhesive covering element, the fixing element and the wedge-shaped guiding element are at least one of moisture absorbing, waterproof and breathable.

8. The device according to claim 1, wherein the wedge-shaped guiding element is self-adhesive on the second surface.

9. The device according to claim 1, wherein the self-adhesive covering element includes an adhesive which is latex-free.

10. The device according to claim 9, wherein the adhesive is hypoallergenic.

11. The device according to claim 1, wherein at least one of the wedge-shaped guiding element, the fixing element and the self-adhesive covering element are formed of at least one of polyurethane, polypropylene and polyethylene.

12. The device according to claim 1, wherein the wedge-shaped guiding element has an angle between 1 degree and 30 degrees.

13. The device according to claim 1, wherein the wedge-shaped guiding element has a recess at the tapered end, and the recess is between two lateral protrusions of the wedge-shaped guiding element.

14. The device according to claim 13, wherein the wedge-shaped guiding element has an opposite end opposite the tapered end, and the recess extends from the tapered end of the wedge-shaped guiding element towards the opposite end of the wedge-shaped guiding element.

15. The device according to claim 14, wherein the recess of the wedge-shaped guiding element narrows in width as the recess extends from the tapered end of the wedge-shaped guiding element towards the opposite end of the wedge-shaped guiding element.

16. The device according to claim 1, wherein at least one of the wedge-shaped guiding element, the fixing element and the self-adhesive covering element are adapted to at least one of a particular catheter size and catheter profile.

17. The device according to claim 16, wherein the at least one of the wedge-shaped guiding element, the fixing element and the self-adhesive covering element are adapted to the at least one of the particular catheter size and the catheter profile by at least one cavity corresponding to the size or the profile of the catheter for receiving an outline of the catheter.

18. The device according to claim 1, wherein the fixing element has at least one of a recess and a cavity on a surface located towards the body for the entry of at least one of the catheter and the wedge-shaped guiding element.

19. The device according to claim 1, wherein the self-adhesive covering element has lateral wings which laterally enclose the catheter at an end opposite to the entry point.

20. The device according to claim 19, wherein the lateral wings laterally enclose the catheter at the end opposite to the entry point in an area where a hose can be connected to the catheter.

21. A device for covering a catheter access of a catheter to a body, comprising:
a wedge-shaped guiding element configured to be arranged between the catheter of the catheter access and a surface of the body, and configured such that the catheter rests on the wedge-shaped guiding element and is supported along a slope of the wedge-shaped guiding element, and wherein the wedge-shaped guiding element is configured to guide the catheter relative to an entry point into the body;
a self-adhesive covering element which covers and fixes the wedge-shaped guiding element and the catheter in an area of the entry point into the body;
wherein at least a portion of the self-adhesive covering element is configured to be adhesively affixed directly to the surface of the body; and
wherein the catheter and the wedge-shaped guiding element are configured to be at least partially arranged between the covering element and the surface of the body; and
a self-adhesive fixing element configured to be arranged between the catheter and the self-adhesive covering element, wherein at least a portion of the self-adhesive fixing element is configured to be adhesively affixed directly to the surface of the body and wherein the fixing element is configured to fix the catheter relative to the entry point and the self-adhesive covering element;
wherein the wedge-shaped guiding element has a tapered end, a length and opposing surfaces, the opposing surfaces comprising a first surface which faces towards the self-adhesive covering element, and a second surface to face towards the surface of the body, and wherein the first and the second surfaces of the wedge-shaped guiding element comprise converging surfaces which converge towards the tapered end along the length of the wedge-shaped guiding element;
wherein the wedge-shaped guiding element has a recess at the tapered end, and the recess is between two lateral protrusions of the wedge-shaped guiding element;
wherein the wedge-shaped guiding element has an opposite end opposite the tapered end, and the recess extends from the tapered end of the wedge-shaped guiding element towards the opposite end of the wedge-shaped guiding element; and
wherein the recess of the wedge-shaped guiding element narrows in width as the recess extends from the tapered end of the wedge-shaped guiding element towards the opposite end of the wedge-shaped guiding element.

22. The device according to claim 21, wherein at least one of the wedge-shaped guiding element, the fixing element and the self-adhesive covering element are at least partially gel-like.

23. The device according to claim 22, wherein the fixing element is gel-like.

24. The device according to claim 23, wherein the fixing element comprises a gel.

25. The device according to claim 21, wherein at least one of the self-adhesive covering element, the fixing element and the wedge-shaped guiding element are at least partially transparent.

26. The device according to claim 21, wherein at least one of the self-adhesive covering element, the fixing element and the wedge-shaped guiding element have at least one of an anti-microbial, anti-bacterial and anti-fungal effect.

27. The device according to claim 21, wherein at least one of the self-adhesive covering element, the fixing element and the wedge-shaped guiding element are at least one of moisture absorbing, waterproof and breathable.

28. The device according to claim 21, wherein the wedge-shaped guiding element is self-adhesive on the second surface.

29. The device according to claim 21, wherein the self-adhesive covering element includes an adhesive which is latex-free.

30. The device according to claim 29, wherein the adhesive is hypoallergenic.

31. The device according to claim 21, wherein at least one of the wedge-shaped guiding element, the fixing element and the self-adhesive covering element are formed of at least one of polyurethane, polypropylene and polyethylene.

32. The device according to claim 21, wherein the wedge-shaped guiding element has an angle between 1 degree and 30 degrees.

33. The device according to claim 21, wherein at least one of the wedge-shaped guiding element, the fixing element and the self-adhesive covering element are adapted to at least one of a particular catheter size and catheter profile.

34. The device according to claim 33, wherein the at least one of the wedge-shaped guiding element, the fixing element and the self-adhesive covering element are adapted to the at least one of the particular catheter size and the catheter profile by at least one cavity corresponding to the size or the profile of the catheter for receiving an outline of the catheter.

35. The device according to claim 21, wherein the fixing element has at least one of a recess and a cavity on a surface located towards the body for the entry of at least one of the catheter and the wedge-shaped guiding element.

36. The device according to claim 21, wherein the self-adhesive covering element has lateral wings which laterally enclose the catheter at an end opposite to the entry point.

37. The device according to claim 36, wherein the lateral wings laterally enclose the catheter at the end opposite to the entry point in an area where a hose can be connected to the catheter.

38. The device according to claim 21, wherein the self-adhesive fixing element is wedge-shaped.

* * * * *